(12) United States Patent
Oba et al.

(10) Patent No.: US 10,876,995 B2
(45) Date of Patent: Dec. 29, 2020

(54) MANUFACTURING METHOD OF GAS SENSOR

(71) Applicant: NGK SPARK PLUG CO., LTD., Nagoya (JP)

(72) Inventors: Takehiro Oba, Konan (JP); Tatsuya Okumura, Kani (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 245 days.

(21) Appl. No.: 15/971,026

(22) Filed: May 4, 2018

(65) Prior Publication Data

US 2019/0004007 A1    Jan. 3, 2019

(30) Foreign Application Priority Data

Jun. 30, 2017   (JP) .................................. 2017-128369

(51) Int. Cl.
| | | |
|---|---|---|
| *G01N 27/407* | (2006.01) | |
| *G01N 27/406* | (2006.01) | |
| *B23P 19/04* | (2006.01) | |
| *G01N 33/00* | (2006.01) | |

(52) U.S. Cl.
CPC .......... *G01N 27/4077* (2013.01); *B23P 19/04* (2013.01); *G01N 27/407* (2013.01); *G01N 27/4062* (2013.01); *G01N 27/4071* (2013.01); *G01N 33/0027* (2013.01); *Y10T 29/49147* (2015.01)

(58) Field of Classification Search
CPC .......... G01N 27/4077; G01N 27/4062; G01N 27/407; G01N 27/4071; G01N 33/0027; B23P 19/04; Y10T 29/49147; Y10T 29/49124; Y10T 29/49117; Y10T 29/49002
USPC .......... 29/842, 829, 825, 592.1; 269/1, 287, 269/288, 315, 900, 903
See application file for complete search history.

(56) References Cited

U.S. PATENT DOCUMENTS

| | | | | |
|---|---|---|---|---|
| 9,612,223 B2 * | 4/2017 | Tahira | ................ | G01N 27/4077 |
| 2002/0138967 A1 * | 10/2002 | Hattori | ............... | G01N 27/4062 29/592 |

FOREIGN PATENT DOCUMENTS

JP        2013-181768 A     9/2013

* cited by examiner

*Primary Examiner* — Peter Dungba Vo
*Assistant Examiner* — Azm A Parvez
(74) *Attorney, Agent, or Firm* — Sughrue Mion, PLLC (57) ABSTRACT

Disclosed is a manufacturing method of a gas sensor. The gas sensor has a plate-shaped sensor element with at least one pair of electrode pads, a separator disposed around the sensor element, and at least one pair of opposed metal terminals held in an insertion hole of the separator and electrically connected at contact regions thereof to the respective electrode pads. The manufacturing method includes mounting the metal terminals in the insertion hole of the separator with the use of a mounting jig. The mounting jig has a flat portion interposed between the contact regions of the metal terminals during the mounting of the metal terminals in the separator so as to prevent contact and entanglement of the opposed metal terminals.

6 Claims, 11 Drawing Sheets

MANUFACTURING METHOD OF GAS SENSOR

FIELD OF THE INVENTION

The present invention relates to a method for manufacturing a gas sensor with a sensor element capable of detecting the concentration of a specific gas component in a gas under measurement. Hereinafter, the term "front" refers to a gas sensing side with respect to the direction of an axis of a gas sensor; and the term "rear" refers to a side opposite the front side.

BACKGROUND OF THE INVENTION

As a gas sensor for detecting the concentration of a specific gas component (such as oxygen or NOx) in an exhaust gas of a vehicle, there is known a gas sensor of the type having a plate-shaped sensor element equipped with a solid electrolyte body. Japanese Laid-Open Patent Publication No. 2013-181768 (FIGS. 1 and 4) discloses one such type of gas sensor that includes: a plate-shaped sensor element having at least one pair of electrode pads on opposite main surfaces of a rear end part thereof; and at least one pair of metal terminals brought into electrical contact with the respective electrode pads so as to take out a sensor output signal from the sensor element. In this gas sensor, the metal terminals have elastically bent portions formed with contact regions, are held in an insertion hole of a separator such that the contact regions of the metal terminals are opposed to each other. When the rear end part of the sensor element is inserted between the opposed contact regions of the metal terminals, the contact regions of the metal terminals are electrically connected to the electrode pads.

SUMMARY OF THE INVENTION

During the mounting of the metal terminals in the separator before the insertion of the sensor element between the metal terminals, there may occur contact and entanglement of the directly opposed metal terminals. This leads to problems such as breakage or deformation of the metal terminal and deterioration of workability.

It is accordingly an object of the present invention to provide a method for manufacturing a gas sensor so as to, during mounting of metal terminals in a separator, suppress breakage or deformation of the metal terminals and attain improvement in workability. The object of the present invention can be achieved by the following aspects.

In accordance with a first aspect of the present invention, there is provided a manufacturing method of a gas sensor, the gas sensor comprising: a plate-shaped sensor element extending in a direction of an axis and having on opposite main surfaces thereof at least one pair of electrode pads; a cylindrical separator formed with an insertion hole and disposed around the sensor element; and at least one pair of metal terminals extending in the direction of the axis and held in the insertion hole of the separator, the metal terminals including bent portions elastically bent at front end sides thereof, the bent portions having contact regions opposed to each other via the sensor element and electrically connected to the respective electrode pads, the manufacturing method comprising mounting the metal terminals in the insertion hole of the separator with the use of a first mounting jig, the first mounting jig having: an installation space in which the separator is installed in the direction of the axis; and a flat portion formed with a predetermined thickness so as to, when the separator and the metal terminals are installed in the installation space, extend from a bottom surface of the installation space toward a rear end side of the separator at a position corresponding to opposed surfaces of the contact regions, said mounting comprising:

a separator installation step of installing the separator in the installation space of the first mounting jig from a rear end side of the first mounting jig so as to place the flat portion in the insertion hole of the separator at the position corresponding to the opposed surfaces of the contact regions;

a metal terminal holding step of inserting and holding the metal terminals into the insertion hole of the separator from a rear end side of the separator so as to interpose the flat portion between opposed surfaces of the contact regions; and a jig detachment step of detaching the first mounting jig frontward relative to the separator.

In the first aspect, the flat portion of the first mounting jig is interposed between the opposed contact regions of the metal terminals during the mounting of the metal terminals in the separator. Thus, the opposed metal terminals are prevented from coming into contact and entanglement with each other. It is consequently possible to suppress breakage or deformation of the metal terminals and attain improvement in workability.

In accordance with a second aspect of the present invention, there is provided a manufacturing method of a gas sensor, the gas sensor comprising: a plate-shaped sensor element extending in a direction of an axis and having on opposite main surfaces thereof at least one pair of electrode pads; a cylindrical separator formed with an insertion hole and disposed around the sensor element; and at least one pair of metal terminals extending in the direction of the axis and held in the insertion hole of the separator, the metal terminals including bent portions elastically bent at front end sides thereof, the bent portions having contact regions opposed to each other via the sensor element and electrically connected to the respective electrode pads, the manufacturing method comprising mounting the metal terminals in the insertion hole of the separator with the use of a second mounting jig, the second mounting jig having: an installation space in which the metal terminals are installed in the direction of the axis at the same positions as holding positions of the metal terminals in the insertion hole of the separator; and a flat portion formed with a predetermined thickness so as to, when the metal terminals are installed in the installation space, extend from a bottom surface of the installation space rearward in the direction of the axis at a position corresponding to opposed surfaces of the contact regions, the installation space having an inner diameter smaller than or equal to a maximum outer diameter of a front end portion of the separator, said mounting comprising:

a lead wire insertion step of inserting lead wires though the insertion hole of the separator such that front end portions of the lead wires protrude from a front end side of the insertion hole;

a metal terminal connection step of electrically connecting the metal terminals to the front end portions of the lead wires;

a metal terminal installation step of installing the metal terminals in the installation space of the second mounting jig from a rear end side of the second mounting jig so as to interpose the flat portion between the opposed surfaces of the contact regions;

a separator contact step of, while pulling the lead wires rearward, bringing a front end of the separator into contact with a rear end of the second mounting jig;

a metal terminal holding step of inserting and holding the metal terminals into the insertion hole of the separator from the front end side of the insertion hole in a state where the front end of the separator is in contact with the rear end of the second mounting jig; and a jig detachment step of detaching the second mounting jig frontward relative to the separator.

In the second aspect, the flat portion of the second mounting jig is interposed between the opposed contact regions of the metal terminals during the mounting of the metal terminals in the separator. Thus, the opposed metal terminals are prevented from coming into contact and entanglement with each other. It is consequently possible to suppress breakage or deformation of the metal terminals and attain improvement in workability.

In the first aspect, the mounting jig may be so configured that, when the separator is installed in the mounting jig in the separator installation step, the flat portion protrudes more toward the rear than the separator.

In this configuration, the opposed metal terminals (contact regions) are separated apart from each other by the flat portion of the mounting jig from the beginning of the insertion of the metal terminals into the insertion hole of the separator in the subsequent metal terminal holding step. It is thus possible to reliably prevent contact and entanglement of the metal terminals.

In the second aspect, the mounting jig may be so configured that, in the separator contact step, the flat portion protrudes more toward the rear than the contact regions.

In this configuration, the opposed metal terminals (contact regions) are separated apart from each other by the flat portion of the mounting jig during the insertion of the metal terminals into the insertion hole of the separator in the subsequent metal terminal holding step. It is thus possible to reliably prevent contact and entanglement of the metal terminals.

In the first and second aspects, the mounting jig and the separator may respectively have a first separator restriction part and a second separator restriction part engageable with each other to restrict circumferential rotation of the separator.

As circumferential rotation of the separator is restricted by engagement of the first and second separator restriction parts, it is possible to reliably prevent the metal terminals from coming into contact and entanglement with each other due to such rotation of the separator.

In the first and second aspects, a thickness of the flat portion may preferably be set smaller than a thickness of the sensor element between the pair of electrode pads.

After the opposed metal terminals (contact regions) are plastically deformed by the flat portion of the mounting jig in a direction that increases a distance between the contact regions, the contact regions are brought into electrical contact with the electrode pads. By this thickness control, it is possible to suppress a deterioration of electrical connection reliability caused by a decrease in contact pressure between the metal terminals and the electrode pads.

In the first and second aspects, the mounting jig may have a metal terminal restriction part protruding from the flat portion and brought into contact with side surfaces of the metal terminals to restrict positional displacement of the metal terminals.

As width-direction movement of the metal terminals is restricted by contact of the metal terminal restriction part with the side surfaces of the metal terminals (intersecting surfaces of the bent portions), it is possible to prevent positional displacement of the metal terminals in the separator (mounting jig).

In the first and second aspects, the gas sensor may have two or more pairs of the metal terminals such that the metal terminals are aligned in an alignment direction along the flat portion and satisfy the following conditions: $GL+GR=W3-W2$, $GL<W1$ and $GR<W1$ where $W1$ is a width of the metal terminal at the contact region; $W2$ is a width of the flat portion in the alignment direction; $W3$ is a maximum width of the insertion hole in the alignment direction; $GL$ is a clearance from one side of the flat portion in the alignment direction to the insertion hole; and $GR$ is a clearance from the other side of the flat portion in the alignment direction to the insertion hole.

In this configuration, the clearance $GL+GR$ between the flat portion and the insertion hole is set smaller than the width $W1$ of the metal terminal. It is thus possible to, even when the metal terminal is displaced in position in the alignment direction, reliably prevent such a displaced metal terminal from moving beyond the flat portion and coming into contact and entanglement with the opposed metal terminal.

As mentioned above, it is possible according to the present invention to effectively suppress breakage or deformation of the metal terminals and attain improvement in workability during the mounting of the metal terminals in the separator.

The other objects and features of the present invention will also become understood from the following description.

DESCRIPTION OF EMBODIMENTS

Hereinafter, the present invention will be described below by way of the following embodiments.

First, a gas sensor 200 to which the present invention is applicable will be explained below with reference to FIGS. 1 to 4. The gas sensor 200 is herein configured as an oxygen sensor for detecting the concentration of oxygen in an exhaust gas of an automotive vehicle or internal combustion engine.

Figure 1:
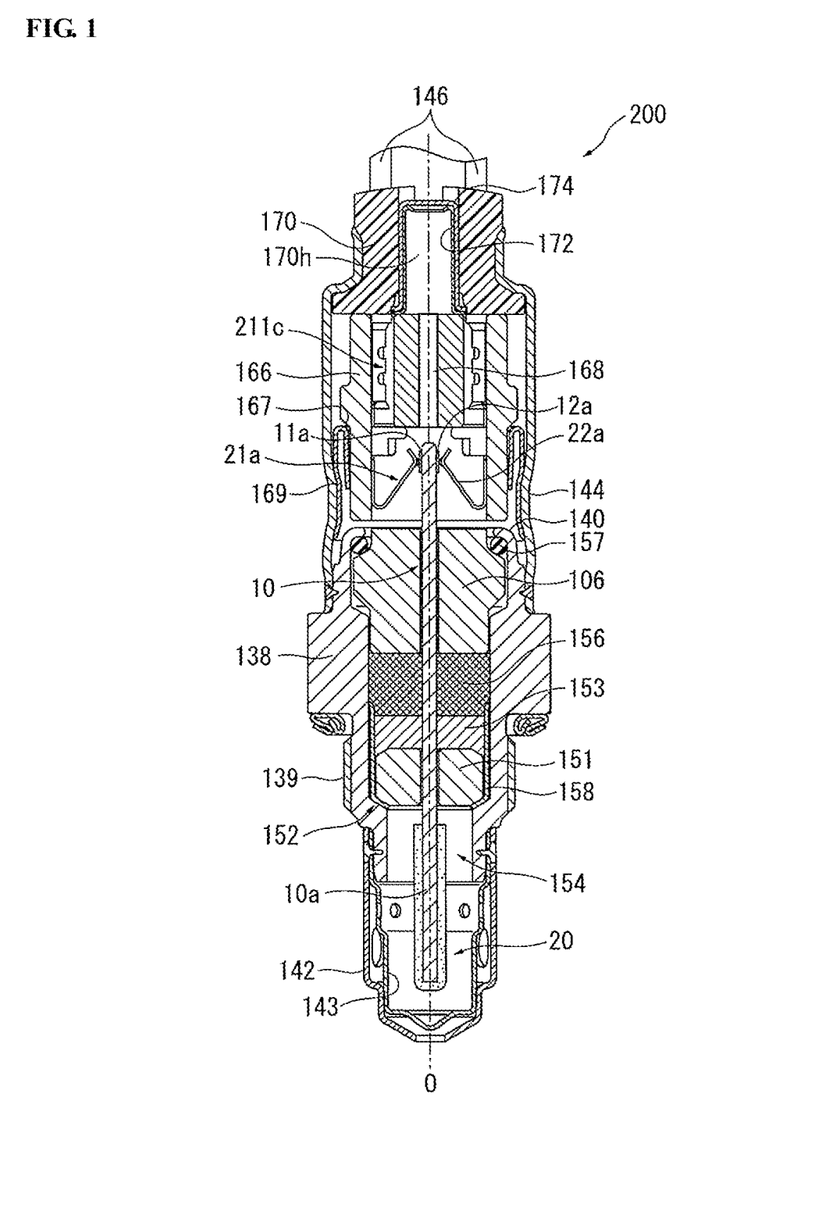
FIG. 1 is a cross-sectional view of a gas sensor to which the present invention is applicable.

FIG. 1 is a cross-sectional view of the gas sensor 200. As shown in FIG. 1, the gas sensor 200 includes: a cylindrical metal shell 138 having on an outer circumferential surface thereof a thread portion 139 for fixing the gas sensor 200 to an exhaust pipe of the vehicle or engine; a sensor element 10 extending in the direction of an axis O (also referred to as "axial direction" or "longitudinal direction"; vertical direction in FIG. 1) of the gas sensor 200; a cylindrical ceramic sleeve 106 arranged to radially surround a circumference of the sensor element 10; a cylindrical separator 166 made of a ceramic material, with an insertion hole 168 formed therethrough in the direction of the axis O, and arranged to surround a rear end part of the sensor element 10 in a front end region of the insertion hole 168; and four metal terminals 21a, 21b, 22a and 22b disposed between the sensor element 10 and the separator 166. (In FIG. 1, only two metal terminals 21a and 22a are illustrated.) A gas sensing portion 10a is provided on the front end part of the sensor element 10 and is covered by a porous protective layer 20 of alumina etc.

The metal shell 138 is made of e.g. stainless steel in a substantially cylindrical shape, with a through hole 154 formed therethrough in the direction of the axis O. The sensor element 10 is situated in the through hole 154 such that the front end part of the sensor element 10 protrudes from a front end of the metal shell 138 and such that the rear end part of the sensor element 10 protrudes from a rear end of the metal shell 138. The metal shell 138 has a step portion 152 radially inwardly protruding in the through hole 154 so as to define an inward tapered surface at a given inclination angle with respect to a plane orthogonal to the axial direction.

An annular ceramic holder 151 of alumina, annular packed layers of talc powder (hereinafter also referred to as talc rings) 153 and 156 and the above-mentioned cylindrical ceramic sleeve 106 are stacked, in this order from the front side to the rear side, within the through hole 154 of the metal shell 138 so as to radially surround the sensor element 10. A metal holder 158 is arranged between the ceramic holder 151 and the step portion 152 of the metal shell 138 so as to hold the talc ring 153 and the ceramic holder 151. A crimp packing 157 is arranged between the ceramic sleeve 106 and a rear end portion 140 of the metal shell 138. The rear end portion 140 of the metal shell 138 is crimped to the ceramic sleeve 106 via the crimp packing 157 so as to push the ceramic sleeve 106 toward the front.

A double-structured metal protector, in which outer and inner protector members 142 and 143 are formed of a metal material (such as stainless steel) with a plurality of gas holes, is welded to the outer circumference of a front end portion of the metal shell 138 so as to cover the protruding front end part (gas sensing portion 10a) of the sensor element 10 as shown in FIG. 1.

An outer tube 144 is joined to the outer circumference of the rear end portion 140 of the metal shell 138. A rubber grommet 170 is fitted in a rear end portion of the outer tube 144. Four lead wires 146 are inserted through lead insertion holes of the rubber grommet 170 and electrically connected to the metal terminals 21a, 21b, 22a and 22b, respectively. (In FIG. 1, only two lead wires 146 and only two lead insertion holes are illustrated.) A through hole 170h is formed through the center of the rubber grommet 170 in the direction of the axis O so as to allow introduction of air as a reference atmosphere. A cylindrical filter fitting 172 is disposed in the through hole 170h. A water-repellent filter 174, which has air permeability but no water permeability, is retained between the through hole 170h and the filter fitting 172 so that the air flows in and out of the gas sensor 200 through the filter 174 within the through hole 170h.

Four electrode pads 11a, 11b, 12a and 12b are disposed on opposite surfaces of the protruding rear end part of the sensor element 10. (In FIG. 1, only two electrode pads 11a and 12a are illustrated.)

The separator 166 is disposed around the protruding rear end part of the sensor element 10 so as to cover the electrode pads 11a, 11b, 12a and 12b. As mentioned above, the separator 166 has a cylindrical shape through which the insertion hole 168 is formed along the axial direction. Further, the separator 166 has a collar portion 167 radially outwardly protruding from on an outer circumferential surface thereof. The separator 166 is retained in the outer tube 144 by contact of the collar portion 167 with the outer tube 144 via a retaining member 169.

The above-mentioned four metal terminals 21a, 21b, 22a and 22b are inserted and held in the insertion hole 168 of the separator 166. Herein, the metal terminals 21a and 22a are opposed to each other via the sensor element 10; and the metal terminals 21b and 22b are opposed to each other via the sensor element 10 (see also FIG. 4). Each of the pair of metal terminals 21a and 22a and the pair of metal terminals 21b and 22b corresponds to the claimed pair of metal terminals. In other words, the gas sensor 200 are provided with two pairs of metal terminals 21a, 21b, 22a and 22b.

Figure 2:
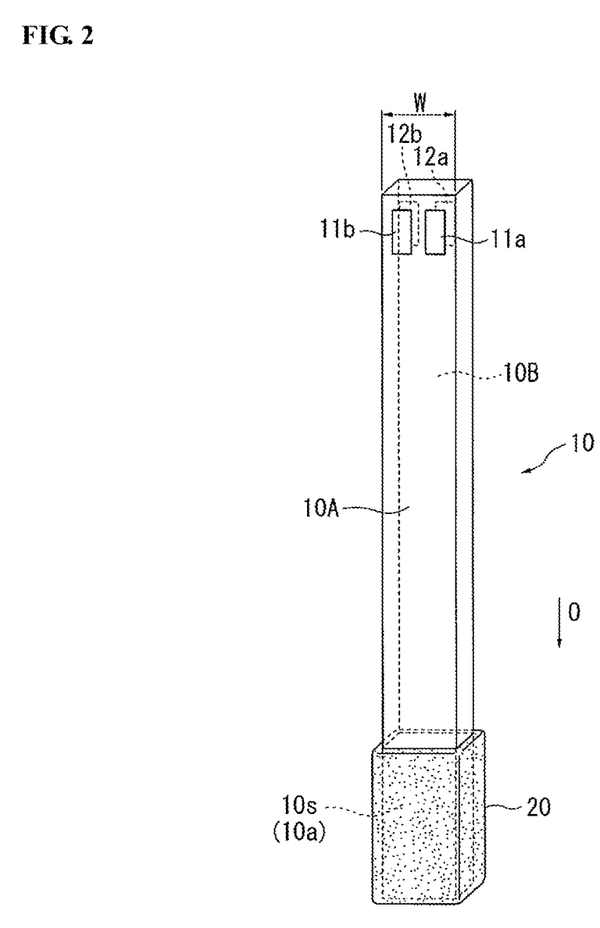
FIG. 2 is a perspective view of a sensor element of the gas sensor.

FIG. 2 is a perspective view of the sensor element 10. As shown in FIG. 2, the sensor element 10 is plate-shaped along the direction of the axis O. The gas sensing portion 10a is formed on the front end part of the sensor element 10 to detect the oxygen concentration of the exhaust gas as mentioned above. Further, the gas sensing portion 10a is covered by the porous protective layer 20. The sensor element 10 itself has a known configuration in which the gas detection sensing portion 10a is provided with an oxygen ion-permeable solid electrolyte body and a pair of electrodes and in which a heater portion is arranged to heat the gas sensing portion 10a and keep the gas sensing portion 10a at a constant temperature although not specifically shown in the drawings.

The two electrode pads 11a and 11b are aligned in a width direction W on one main surface 10A of the rear end part of the sensor element 10. A sensor output signal from the gas sensing portion 10a is taken across the electrode pads 11a and 11b through a lead portion (not shown). On the other hand, the two electrode pads 12a and 12b are aligned in the width direction W on the other main surface 10B of the rear end part of the sensor element 10. The heater portion is energized through a lead portion (not shown) and the electrode pads 12a and 12b.

Each of the electrode pads 11a, 11b, 12a and 12b is elongated rectangular-shaped along the direction of the axis O. These electrode pads 11a, 11b, 12a and 12b can be each provided as a sintered compact containing e.g. Pt as a main component. The electrode pads 11a and 11b on the main surface 10A are opposed to the electrode pads 12a and 12b on the main surface 10B, respectively, via the sensor element 10. Namely, the electrode pads 11a and 12a are paired and opposed to each other via the sensor element 10; and the electrode pads 11b and 12b are paired and opposed to each other via the sensor element 10. In other words, the gas sensor 200 are provided with two pairs of electrode pads 11a, 11b, 12a and 12b.

Figure 3:
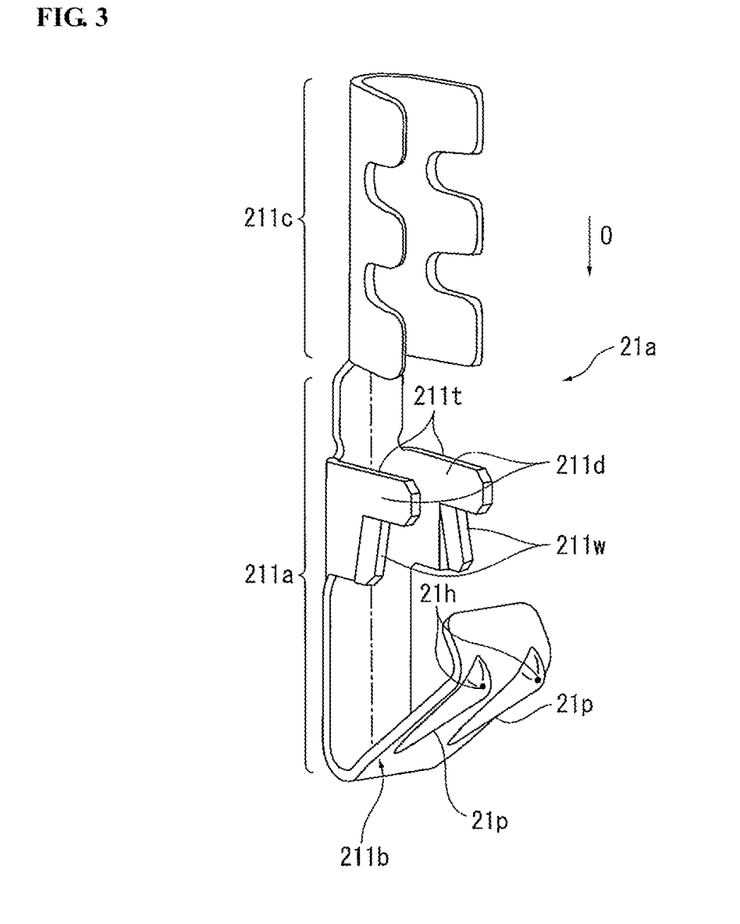
FIG. 3 is a perspective view of a metal terminal of the gas sensor.

FIG. 3 is a perspective view of the metal terminal 21a. As the metal terminals 21a, 21b, 22a and 22b are the same in shape and size, the metal terminal 21a will be representatively explained in detail below. It is needless to say that the same explanation applies to the metal terminals 21b, 22a and 22b. As shown in FIG. 3, the metal terminal 21a integrally includes: a substantially plate-shaped body portion 211a extending in the direction of the axis O; a bent portion 211b bent rearward to extend from a front end of the body portion 211a to one side (i.e. sensor element 10 side); a crimp terminal portion 211c extending from a rear end of the body portion 211a toward the rear; and a pair of stopper portions 211d bent perpendicular to the direction of the axis O to extend in the same direction as the bent portion 211b from substantially axially middle positions on both sides of the body portion 211a. For example, the metal terminal 21a can be produced in one piece by die-cutting a single sheet of metal plate and bend-forming the bent portion 211b and the stopper portions 211d. The production method of the metal terminal 21a is however not limited to such a procedure.

As is conventionally known, the crimp terminal portion 211c is cylindrical-shaped and electrically connected to the lead wire 146 by inserting an exposed conductor portion of the lead wire 146 in the crimp terminal portion 211c and crimping the crimp terminal portion 211c onto the exposed conductor portion of the lead wire 146.

A distal free end of the bent portion 211b is bent toward the rear. Two contact regions 21p are provided on a surface of the bent portion 211b (opposite from a surface of the bent portion 211b facing the body portion 211a). These contact regions 21p are arranged in a width direction and each formed in a protrusion shape such that apexes 21h of the contact regions 21p are brought into point contact with the electrode pad 11a. As the bent portion 211b with the contact regions 21p is pressed onto and held in contact with the electrode pad 11a under the spring force (elasticity) of the metal terminal 21a, electrical connection is reliably established between the metal terminal 21a and the electrode pad 11a.

Figure 4:
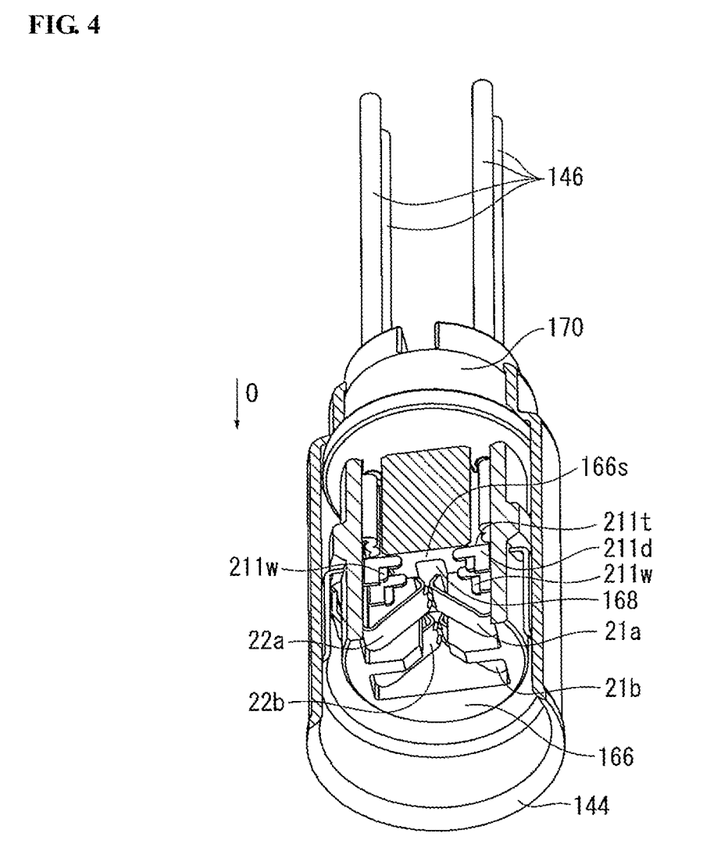
FIG. 4 is a perspective sectional view of a state in which the metal terminals are mounted in a separator.

FIG. 4 is a perspective sectional view of a state in which the metal terminals 21a, 21b, 22a and 22b are mounted in the separator 166. The metal terminals 21a, 21b, 22a and 22b are held in the separator 166, in a state of being separated apart and kept from contact with each other, so as to face the insertion hole 168 of the separator 166 as shown in FIG. 4. More specifically, four terminal installation holes 168a to 168d (see also FIG. 7) are formed in the separator 166 along the direction of the axis O. The terminal members 21a, 21b, 22a and 22b are held in the respective terminal installation holes 168a to 168d and thereby kept from contact with each other.

When the terminal member 21a (21b, 22a, 22b) is inserted into the terminal installation hole 168a (168b, 168c, 168d) of the separator 166 from the front end side, rear-facing surfaces 211t of the pair of stopper portions 211d are brought into contact with a front-facing surface 166s of the separator 166. By contact of the rear-facing surfaces 211t of the stopper portions 211d with the front-facing surface 166s of the separator 166, the terminal member 21a (21b, 22a, 22b) is prevented from falling off toward the rear from the front-facing surface 166s of the separator 166 and is fixed in position in the direction of the axis O.

Furthermore, cuts are made in plate surfaces of the stopper portions 211d from their respective front edges toward the rear so as to form strip-shaped engaging portions 211w as shown in FIG. 3. The engaging portions 211w extend outwardly and toward the front from the plate surfaces of the stopper portions 211d. When the terminal member 21a (21b, 22a, 22b) is inserted into the terminal installation hole 168a (168b, 168c, 168d) of the separator 166, the engaging portions 211w are engaged with opposed wall surfaces of the terminal installation hole 168a (168b, 168c, 168d). By engagement of the engaging portions 211 with the opposed wall surfaces of the terminal installation hole 168a (168b, 168c, 168d), the terminal member 21a (21b, 22a, 22b) is fixed in position in a direction perpendicular to the axis O.

As shown in FIG. 4, the contact regions 21p of the pair of metal terminals 21a and 22a are opposed to each other; and the contact regions 21p of the other pair of metal terminals 21b and 22b are opposed to each other. Although the opposed contact regions 21p are in contact with each other before the insertion of the sensor element 10 in this illustrated example, the opposed contact regions 21p may alternatively be spaced apart from each other in a state before the insertion of the sensor element 10.

Figure 5:
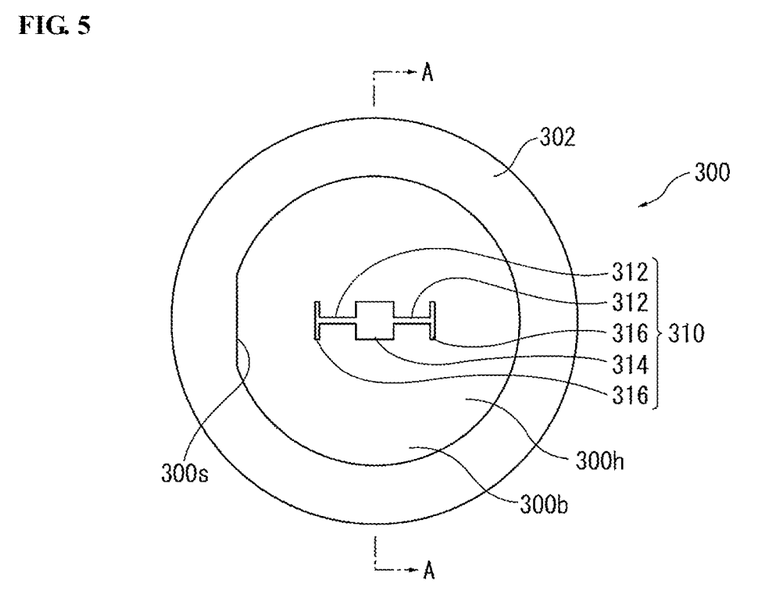
FIG. 5 is a plan view of a first mounting jig used in a manufacturing method of the gas sensor according to a first embodiment of the present invention.
Figure 6:
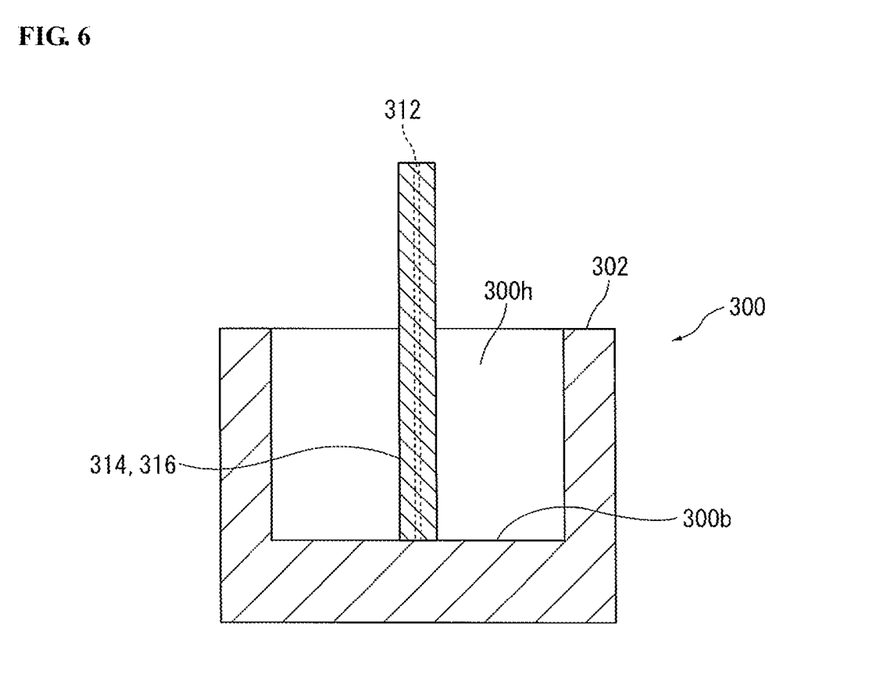
FIG. 6 is a cross-sectional view of the first mounting jig taken along line A-A of FIG. 5.
Figure 7:
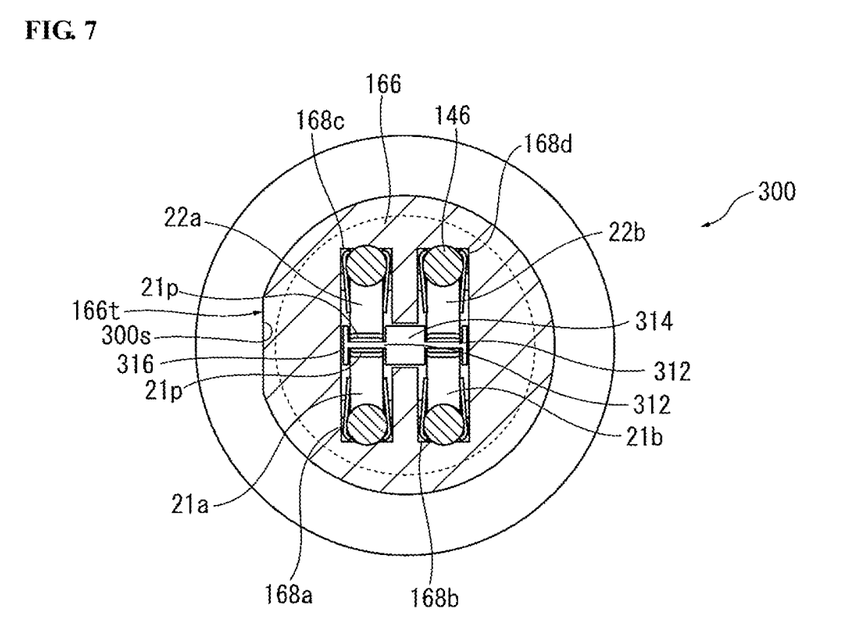
FIG. 7 is a schematic view of a state in which the metal terminals are inserted and held in the separator installed in the first mounting jig.

Next, a manufacturing method of the gas sensor 200 according to a first embodiment of the present invention will be explained below with reference to FIGS. 5 to 8. In the first embodiment, the metal terminals 21a, 21b, 22a and 22b are mounted in the separator 160 with the use of a first mounting jig 300. FIG. 5 is a schematic view of the first mounting jig 300. FIG. 6 is a cross-sectional view of the first mounting jig 300 taken along line A-A of FIG. 5. FIG. 7 is a schematic view showing a state in which the metal terminals 21a, 21b, 22a and 22b are inserted and held in the separator 166 installed in the first mounting jig 300. FIGS. 8A to 8D are schematic views of the manufacturing method of the gas sensor 200 according to the first embodiment.

As shown in FIGS. 5 and 6, the first mounting jig 300 has a bottomed cylindrical shape in which a cylindrical installation space 300h is defined through the center of the first mounting 300 to be open at an upper side thereof. A protrusion 310 is formed on the first mounting jig 300 so as to extend upward from the center of a bottom surface 300b of the installation space 300h and protrude more upward than an upper surface 302 of the first mounting jig 300. This protrusion 300 is located at a such position as to, when the separator 166 is installed in the installation space 300h, correspond to the insertion hole 168 of the separator 166 as shown in FIG. 7. The first mounting jig 300 (including the protrusion 310) can be made of e.g. a metal material such as stainless steel.

In the first embodiment, the protrusion 310 is substantially H-shaped when viewed from the upper side as shown in FIG. 5. More specifically, the protrusion 310 includes: a rectangular column portion 314 located in the center thereof; two plate-shaped flat portions 312 extending in opposite directions from opposite surfaces of the rectangular column portion 314; and two lateral wall portions 316 extending from respective ends of the flat portions 312 in directions perpendicular to the flat portions 312 and each having both ends in flush with the other two opposite surfaces of the rectangular column portion 314. The rectangular column portion 314 and the lateral wall portions 316 protrude from plate surfaces of the flat portion 312. The two flat portions 312 are located at such positions as to, when the metal terminals 21a, 21b, 22a and 22b are inserted in the separator 166 installed in the installation space 300h, correspond to opposed surfaces of the contact regions 21p of the pair of metal terminals 21a and 22a and the pair of metal terminals 21b and 22b as shown in FIG. 7.

As shown in FIGS. 5 and 7, a part of the outer circumference of the installation space 300h is formed as a straight portion 300s; and a straight portion 166t is formed on the separator 166 so as to be engageable with the straight portion 300s. By engagement of the straight portions 300s and 166t, the separator 166 is restricted from rotating in the circumferential rotation as will be explained below. The straight portions 300s and 166t thus correspond to the claimed first and second separator restriction parts in the first embodiment.

Further, the rectangular column portion 314 and the lateral wall portions 316 serve together to restrict positional displacement of the metal terminals 21a, 21b, 22a and 22b as will be explained below and thus correspond to the claimed metal terminal restriction part in the first embodiment.

The manufacturing method of the gas sensor 200 according to the first embodiment includes a separator installation step, a metal terminal holding step and a jig detachment step in this order as shown in FIGS. 8A to 8D. In FIGS. 8A to 8D, only the pair of metal terminals 21a and 22a is illustrated because the pair of metal terminals 21b and 22b is located behind the pair of metal terminals 21a and 22a. Although the following explanation will be representatively given to the pair of metal terminals 21a and 22a, the same explanation applies to the pair of metal terminals 21b and 22b.

Figures 8A, 8B:
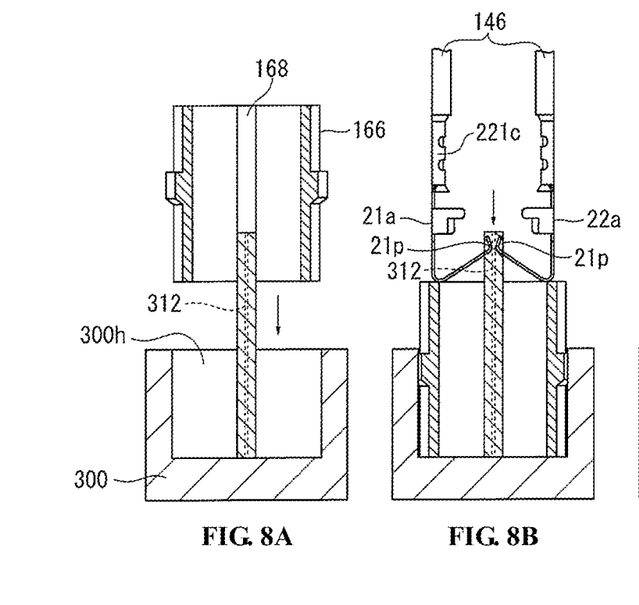
FIGS. 8A to 8D are schematic views of the manufacturing method of the gas sensor according to the first embodiment of the present invention.

In the separator installation step, the separator 166 is installed in the installation space 300h of the first mounting jig 300 from the upper side (rear end side) in the axial direction. Then, the flat portions 312 of the first mounting jig 300 are placed in the insertion hole 168 of the separator 166 at such positions as to correspond to the opposed surfaces of the contact regions 21p as shown in FIGS. 8A and 8B.

In the metal terminal holding step, the metal terminals 21a and 22a are inserted and held into the terminal installation holes 168a and 168c of the separator 166 from the rear end side. At this time, the flat portion 312 is interposed between the opposed surfaces of the contact regions 21p of the metal terminals 21a and 22a as shown in FIGS. 7, 8B and 8C.

In the first embodiment, the lead wires 146 have previously been connected by crimping to the crimp terminal portions 211c of the metal terminals 21a and 22a.

Figures 8C, 8D:
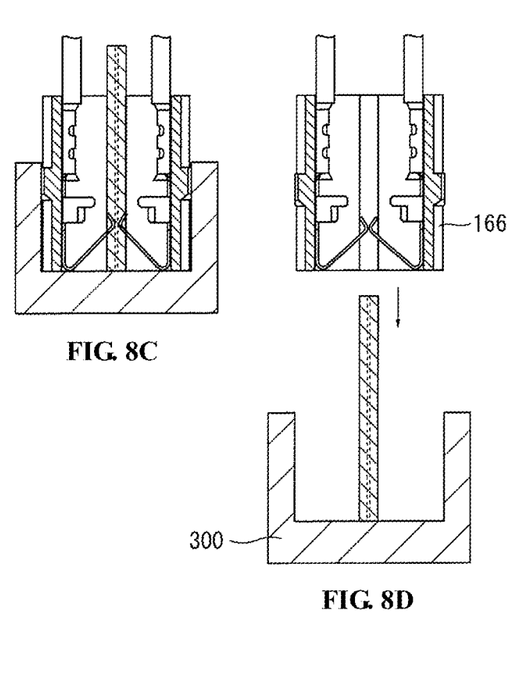

In the jig detachment step, the first mounting jig 300 is detached toward the front end side (bottom side) relative to the separator 166 as shown in FIG. 8D.

As explained above, the flat portion 312 of the first mounting jig 300 is interposed between the opposed contact regions 21p of the pair of metal terminals 21a and 22a (21b and 22b) during the mounting of the metal terminals 21a and 22a (21b and 22b) in the separator 166 in the first embodiment. Thus, the opposed metal terminals 21a and 22a (21b and 22b) are prevented from coming into contact and entanglement with each other. It is consequently possible to suppress breakage or deformation of the metal terminals 21a and 22a (21b and 22b) and attain improvement in workability.

The flat portion 312 is formed to, when the separator 166 is installed in the first mounting jig 300 in the separator installation step, protrude more rearward than the rear end of the separator 166 as shown in FIG. 8B in the first embodiment. In this configuration, the opposed contact regions 21p of the metal terminals 21a and 22a (21b and 22b) are separated apart from each other by the flat portion 312 from the beginning of the insertion of the metal terminals 21a and 22a (21b and 22b) into the separator 166 in the subsequent metal terminal holding step. It is thus possible to reliably prevent contact and entanglement of the metal terminals 21a and 22a (21b and 22b).

As shown in FIGS. 5 and 7, the straight portions 300s and 166t are respectively formed on the first mounting jig 300 and the separator 166 in the first embodiment. By engagement of these straight portion 300s and 166t, it is possible to prevent the separator 166 from rotating in the circumferential direction in the first mounting jig 300 so that the metal terminals 21a and 22a (21b and 22b) do not come into contact and entanglement with each other due to such rotation of the separator 166.

Preferably, a thickness of the flat portion 312 is set smaller than a thickness of the sensor element 10 between the pair of electrode pads 11a and 12a (11b and 12b) in the first embodiment. After the opposed metal terminals 21a and 22a (21b and 22b) are plastically deformed by the flat portion 312 of the first mounting jig 300 in a direction that increases a distance between the contact regions 21p, the contact regions 21p are brought into electrical contact with the electrode pads 11a and 12a (11b and 12b). By this thickness control, it is possible to suppress a deterioration of electrical connection reliability caused by a decrease in contact pressure between the metal terminals 21a and 22a (21b and 22b) and the electrode pads 11a and 12a (11b and 12b).

Moreover, the rectangular column portion 314 and the lateral wall portions 316 come into contact with respective side surfaces of the metal terminals 21a and 22a (21b and 22b) (intersecting the surfaces of the bent portions 211b on which the contact regions 21p are formed) during the insertion of the metal terminals 21a and 22a into the separator 166. By such contact, it is possible to restrict movement of the metal terminals 21a and 22a (21b and 22b) in the width direction and thereby prevent positional displacement of the metal terminals 21a and 22a (21b and 22b) in the separator 166 (first mounting jig 300).

Figure 9:
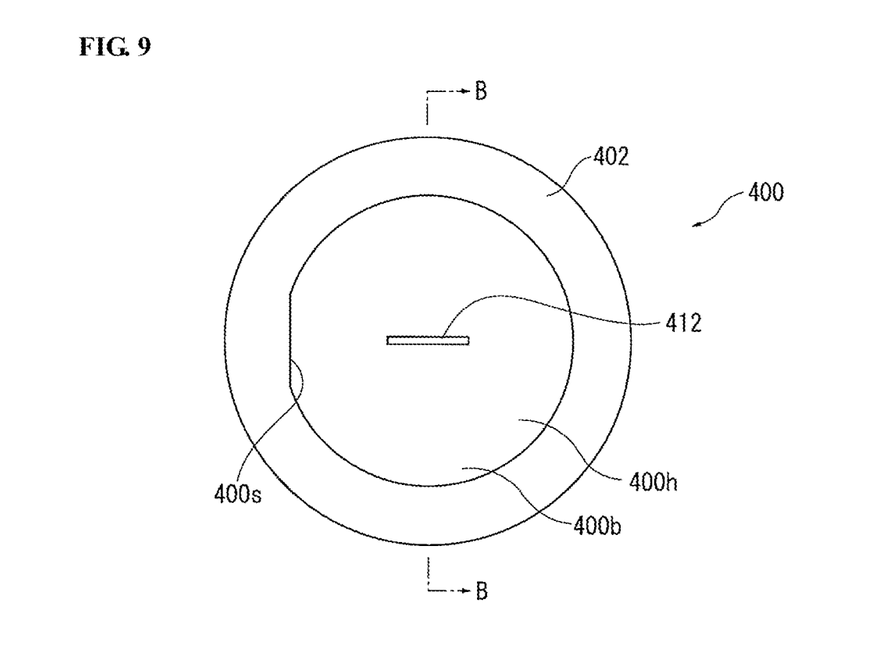
FIG. 9 is a plan view of a second mounting jig used in a manufacturing method of the gas sensor according to a second embodiment of the present invention.
Figure 10:
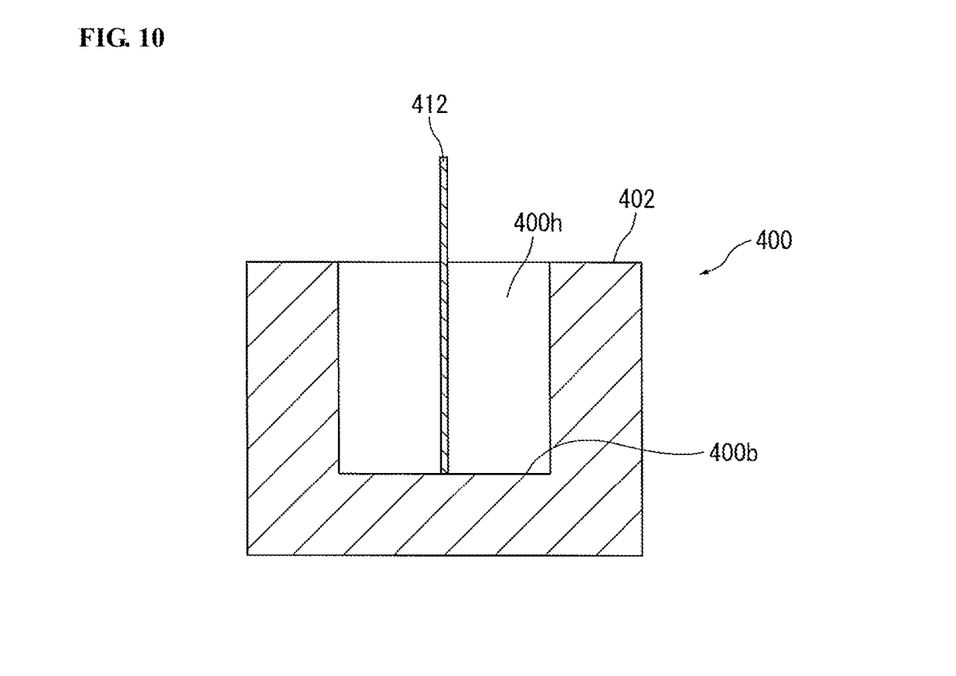
FIG. 10 is a cross-sectional view of the second mounting jig taken along line B-B of FIG. 9.
Figure 11:
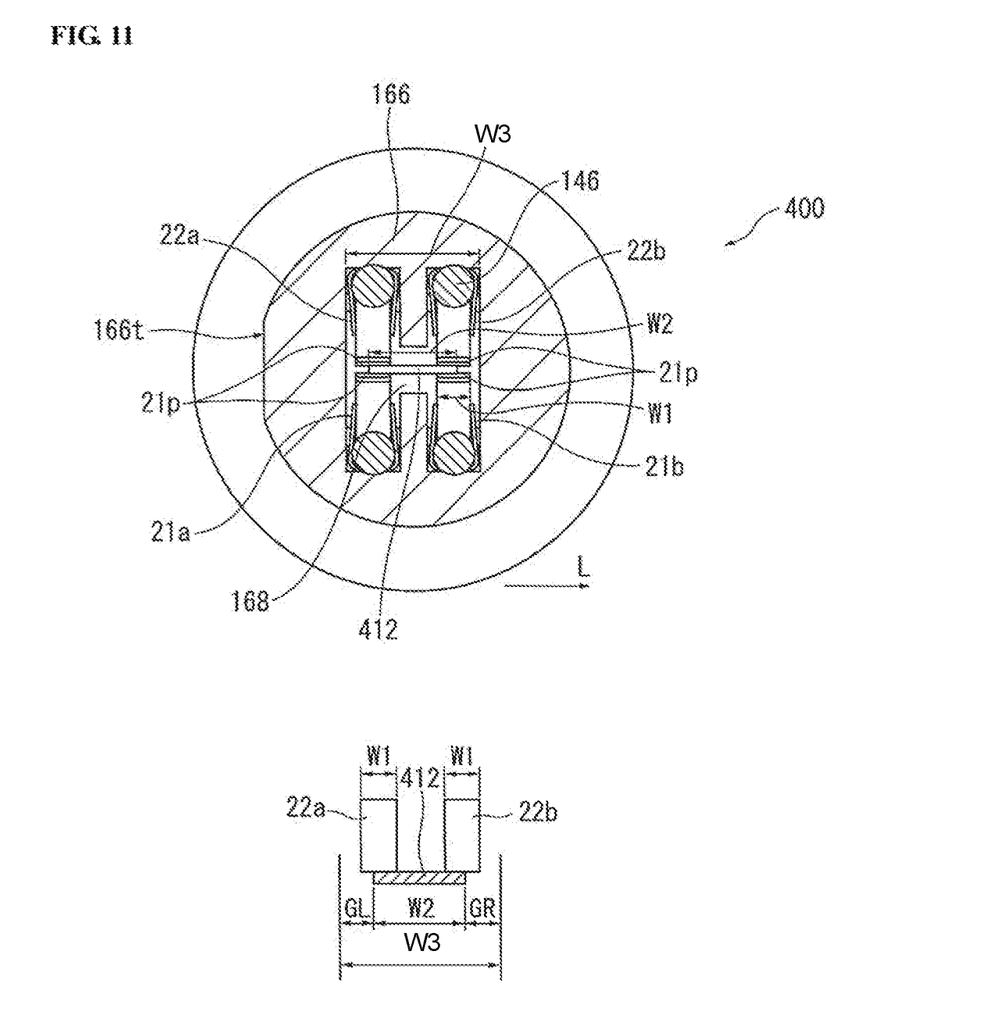
FIG. 11 is a schematic view of a state in which the metal terminals are installed in the second mounting jig.

A manufacturing method of the gas sensor 200 according to a second embodiment of the present invention will be next explained below with reference to FIGS. 9 to 13. In the second embodiment, the metal terminals 21a, 21b, 22a and 22b are mounted in the separator 160 with the use of a second mounting jig 400. FIG. 9 is a schematic view of the second mounting jig 400. FIG. 10 is a cross-sectional view of the second mounting jig 400 taken along line B-B of FIG. 9. FIG. 11 is a schematic view of a state in which metal terminals 21a, 21b, 22a and 22b are installed in the second mounting jig 400. FIGS. 12A to 12E are schematic views of the manufacturing method of the gas sensor 200 according to the second embodiment. FIG. 13 is a schematic view of a state in which the metal terminals 21a, 21b, 22a and 22b are displaced in position relative to a flat portion 412 of the second mounting jig 400.

As shown in FIGS. 9 and 10, the second mounting jig 400 has a bottomed cylindrical shape in which a cylindrical installation space 400h is defined through the center of the second mounting jig 400 to be open at an upper side thereof. The flat portion 412 is formed in a plate shape on the second mounting jig 400 so as to extend upward from the center of a bottom surface 400b of the installation space 400h and protrude more upward than an upper surface 402 of the second mounting jig 400. This flat portion 412 is located at such a position as to, when the separator 166 and the metal terminals 21a, 21b, 22a and 22b are installed in the installation space 400h, correspond in position to the insertion hole 168 of the separator 166 and to the opposed surfaces of the contact regions 21p of the pairs of metal terminals 21a and 22a and metal terminals 21b and 22b as shown in FIG. 11. The second mounting jig 400 (including the flat portion 12) can be made of e.g. a metal material such as stainless steel.

As shown in FIGS. 9 and 11, a part of the outer circumference of the installation space 400h is formed as a straight portion 400s; and a straight portion 166t is formed on the separator 166 so as to be engageable with the straight portion 400s. By engagement of the straight portions 400s and 166t, the separator 166 is restricted from rotating in the circumferential rotation as in the case of the straight portions 300s and 166t. The straight portions 400s and 116 thus correspond to the claimed first and second separator restriction parts in the second embodiment.

When the metal terminals 21a, 21b, 22a and 22b are installed in the installation space 400h of the second mounting jig 400 so that the flat portion 412 is interposed between the contact regions 21p of the metal terminals 21a, 21b, 22a and 22b in the after-mentioned metal terminal installation step, the metal terminals 21a and 21b are aligned on one main surface of the flat portion 412; and the metal terminals 22a and 22b are aligned on the other main surface of the flat portion 412 as shown in FIG. 11. Herein, the direction of alignment of the metal terminals (i.e. the direction of the main surfaces of the flat portion 412) is referred to as "alignment direction L". It is defined that: W1 is a width of the metal terminal 21a, 21b, 22a, 22b at the contact region 21p; W2 is a width of the main surface of the flat portion 412; W3 is a maximum width of the insertion hole 168 of the separator 166 in the alignment direction L; GL is a clearance from the left side of the flat portion 412 in the alignment direction L to the insertion hole 168; and GR is a clearance from the right side of the flat portion 412 in the alignment direction L to the insertion hole 168.

In the second embodiment, the total width (2×W1) of the two aligned metal terminals 21a and 21b (22a and 22b) in the alignment direction L is preferably set smaller than the width W2 of the flat portion 412. It is possible by satisfaction of the condition: (2×W1)<W2 to, even when the metal terminal 21a, 21b, 22a, 22b is displaced in the alignment direction L as shown in FIG. 13, reliably prevent the displaced metal terminal from moving beyond the flat portion 412 and coming into contact and entanglement with the opposed metal terminal.

Moreover, the metal terminals 21a, 21b, 22a and 22b, the separator 166 and the second mounting jig 412 are preferably be configured to satisfy the following conditions: GL+GR=W3−W2; GL<W1; and GR<W1. In this configuration, the clearance GL+GR between the flat portion 412 and the insertion hole 168 is set smaller than the width W1 of the metal terminal 21a, 21b, 22a, 22b so that the metal terminal 21a, 21b, 22a, 22b does not pass through the clearance GL, GR and move beyond the flat portion 412. It is possible by satisfaction of the conditions: GL+GR=W3−W2; GL<W1; and GR<W1 to, even when the metal terminal 21a, 21b (22a, 22b) is displaced in position in the alignment direction L, reliably prevent such a displaced metal terminal 21a, 21b (22a, 22b) from coming into contact and entanglement with the opposed metal terminal 22a, 22b (21a, 22b) beyond the flat portion 412.

The manufacturing method of the gas sensor 200 according to the second embodiment includes a lead wire insertion step, a metal terminal connection step, a metal terminal installation step, a separator contact step, a metal terminal holding step and a jig detachment step in this order as shown in FIGS. 12A to 12E. In FIGS. 12A to 12E, only the pair of metal terminals 21a and 22a is illustrated because the pair of metal terminals 21b and 22b is located behind the pair of metal terminals 21a and 22a. Although the following explanation will be representatively given to the pair of metal terminals 21a and 22a, the same explanation applies to the pair of metal terminals 21b and 22b.

In the lead wire insertion step, the lead wires 146 are inserted though the insertion hole 168 of the separator 166 such that front end portions of the lead wires 146 protrude from the front end side of the insertion hole 168.

Figures 12A, 12B:
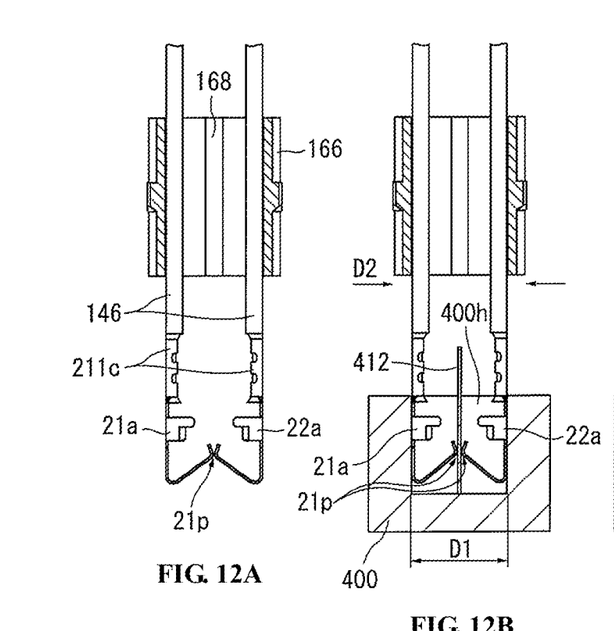
FIGS. 12A to 12E are schematic views of the manufacturing method of the gas sensor according to the second embodiment of the present invention.
Figure 13:
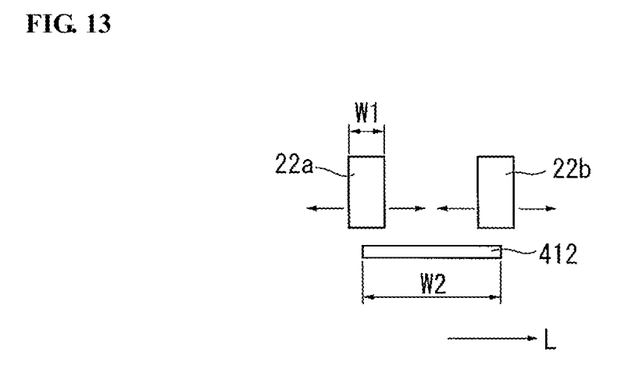
FIG. 13 is a schematic view of a state in which the metal terminal is displaced in position relative to a flat portion of the mounting jig.

In the metal terminal connection step, the crimp terminal portions 211c of the metal terminals 21a and 22a are fixed by crimping (and thereby electrically connected) to the front end portions of the lead wires 146 as shown in FIG. 12A.

In the metal terminal installation step, the metal terminals 21a and 22a are installed in the installation space 400h of the second mounting jig 400 from the upper end side (rear end side) at the same positions as the holding positions of the metal terminals 21a and 22a in the separator 166. At this time, the flat portion 412 of the second mounting jig 400 is inserted and interposed between the opposed surfaces of the contact regions 21p of the metal terminals 21a and 22a as shown in FIG. 12B.

Figure 12C:
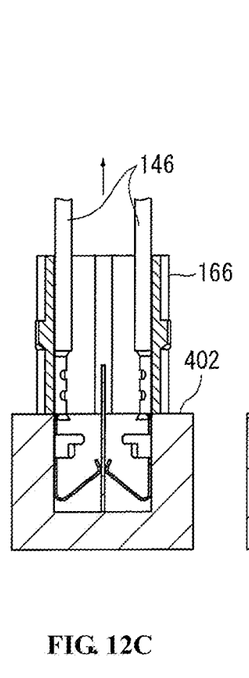

In the separator contact step, a front end of the separator 166 is brought into contact with the rear end (upper surface) 402 of the second mounting jig 400 while the lead wires 146 are pulled rearwards as shown in FIG. 12C. For such contact, an inner diameter D1 of the installation space 400h is set smaller than or equal to a maximum outer diameter D2 of the front end portion of the separator 166 as shown in FIGS. 12B and 12C in the second embodiment.

Figures 12D, 12E:
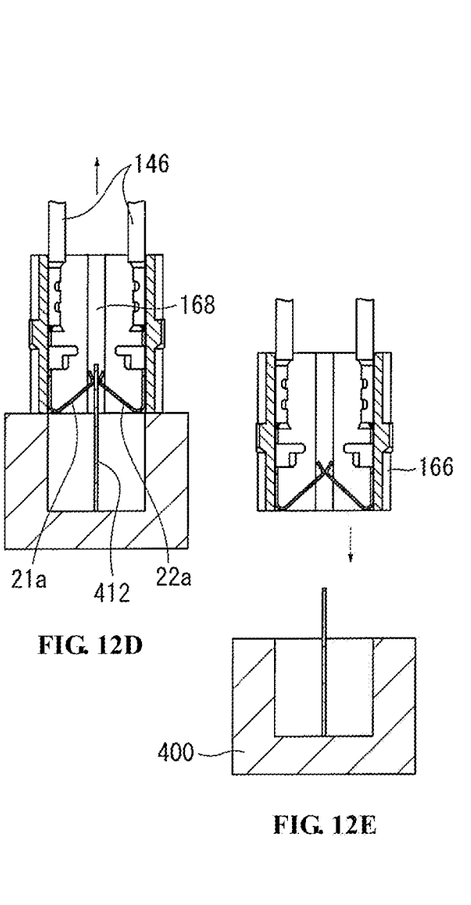

Then, the metal terminals 21a and 22a are inserted and held into the terminal installation holes 168a to 168d from the front end side of the separator 166 in the metal terminal holding step as shown in FIG. 12D.

After that, the second mounting jig 400 is detached toward the front end side (bottom side) relative to the separator 166 as shown in FIG. 12E in the jig detachment step.

As explained above, the flat portion 412 of the second mounting jig 400 is interposed between the opposed contact regions 21p of the pair of metal terminals 21a and 22a (21b and 22b) during the mounting of the metal terminals 21a and 22a (21b and 22b) in the separator 166 in the second embodiment as in the case of the first embodiment. Thus, the opposed metal terminals 21a and 22a (21b and 22b) are prevented from coming into contact and entanglement with each other. It is consequently possible to suppress breakage or deformation of the metal terminals 21a and 22a (21b and 22b) and attain improvement in workability.

In the second embodiment, the flat portion 412 is formed to protrude more rearward than the contact regions 21p in the separator contact step as shown in FIG. 12D. In this configuration, the opposed contact regions 21p of the metal terminals 21a and 22a (21b and 22b) are separated apart from each other by the flat portion 412 during the mounting of the metal terminals 21a and 22a (21b and 22b) in the separator 166. It is thus possible to reliably prevent contact and entanglement of the metal terminals 21a and 22a (21b and 22b).

Further, it is possible by engagement of the straight portion 400s and 166t to prevent the separator 166 from rotating in the circumferential direction in the second mounting jig 400 so that the metal terminals 21a and 22a (21b and 22b) do not come into contact and entanglement with each other due to such rotation of the separator 166.

As in the case of the first embodiment, a thickness of the flat portion 412 is set smaller than a thickness of the sensor element 10 between the pair of electrode pads 11a and 12a (11b and 12b) in the second embodiment. By this thickness control, it is possible to suppress a deterioration of electrical connection reliability caused by a decrease in contact pressure between the metal terminals 21a and 22a (21b and 22b) and the electrode pads 11a and 12a (11b and 12b).

Although the present invention has been described above with reference to the specific exemplary embodiments, the present invention is not limited to the above-described exemplary embodiments. Various modifications and variations of the embodiments described above will occur to those skilled in the art in light of the above teachings.

There are no particular limitations of the shapes of the first or second mounting jig and the metal terminals. For example, the first mounting jig 300 may be configured to satisfy the condition: (2×W1)<W2 and/or to satisfy the conditions: GL+GR=W3−W2; GL<W1; and GR<W1 as in the case of the second mounting jig 400. The second mounting jig 400 may have any portion (as the claimed metal terminal restriction part) protruding from the flat portion 412 and brought into contact with the respective side surfaces of the metal terminals 21a and 22a (21b and 22b) to restrict movement of the metal terminals 21a and 22a (21b and 22b) in the width direction and thereby prevent positional displacement of the metal terminals 21a and 22a (21b and 22b) as in the case of the first mounting jig 300.

There is no particular limitation on the number of pairs of metal terminals. The gas sensor may be provided with only one pair of metal terminals or two or more pairs of metal terminals.

The present invention can be applied to various types of gas sensors such as not only an oxygen sensor and a universal gas sensor but also a NOx sensor etc.

The entire contents of Japanese Patent Application No. 2017-128369 (filed on Jun. 30, 2017) are herein incorporated by reference. The scope of the invention is defined with reference to the following claims.

What is claimed is:

1. A manufacturing method of a gas sensor,
the gas sensor comprising:
a plate-shaped sensor element extending in a direction of an axis and having on opposite main surfaces thereof at least one pair of electrode pads;
a cylindrical separator formed with an insertion hole and disposed around the sensor element; and
at least one pair of metal terminals extending in the direction of the axis and held in the insertion hole of the separator, the metal terminals including bent portions elastically bent at front end sides thereof, the bent portions having contact regions opposed to each other via the sensor element and electrically connected to the respective electrode pads,
the manufacturing method comprising mounting the metal terminals in the insertion hole of the separator with use of a mounting jig,
the mounting jig having: an installation space in which the metal terminals are installed in the direction of the axis at same positions as holding positions of the metal terminals in the insertion hole of the separator; and a flat portion formed with a predetermined thickness so as to, when the metal terminals are installed in the installation space, extend from a bottom surface of the installation space rearward in the direction of the axis at a position corresponding to opposed surfaces of the contact regions, the installation space having an inner diameter smaller than or equal to a maximum outer diameter of a front end portion of the separator,
said mounting comprising:
a lead wire insertion step of inserting lead wires though the insertion hole of the separator such that front end portions of the lead wires protrude from a front end side of the insertion hole;
a metal terminal connection step of electrically connecting the metal terminals to the front end portions of the lead wires;
a metal terminal installation step of installing the metal terminals in the installation space of the mounting jig from a rear end side of the mounting jig so as to interpose the flat portion between the opposed surfaces of the contact regions;
a separator contact step of, while pulling the lead wires rearward, bringing a front end of the separator into contact with a rear end of the mounting jig;
a metal terminal holding step of inserting and holding the metal terminals into the insertion hole of the separator from the front end side of the insertion hole in a state where the front end of the separator is in contact with the rear end of the mounting jig; and
a jig detachment step of detaching the mounting jig frontward relative to the separator.

2. The manufacturing method according to claim 1, wherein, in the separator contact step, the flat portion protrudes more rearward than the contact regions.

3. The manufacturing method according to claim 1, wherein the mounting jig and the separator respectively have a first separator restriction part and a second separator restriction part engageable with each other to restrict circumferential rotation of the separator.

4. The manufacturing method according to claim 1, wherein a thickness of the flat portion is smaller than a thickness of the sensor element between the pair of electrode pads.

5. The manufacturing method according to claim 1, wherein the mounting jig has a metal terminal restriction part protruding from the flat portion and brought into contact with side surfaces of the metal terminals to restrict positional displacement of the metal terminals.

6. The manufacturing method according to claim 1, wherein the gas sensor comprises two or more pairs of the metal terminals such that the metal terminals are aligned in an alignment direction along the flat portion, and
wherein the following conditions are satisfied: GL+GR=W3−W2; GL<W1; and GR<W1 where W1 is a width of the metal terminals at the contact regions; W2 is a width of the flat portion in the alignment direction; W3 is a maximum width of the insertion hole in the alignment direction; GL is a clearance from one side of the flat portion in the alignment direction to the insertion hole; and GR is a clearance from the other side of the flat portion in the alignment direction to the insertion hole.

* * * * *